US012678546B2

(12) United States Patent
Ghahramani

(10) Patent No.: US 12,678,546 B2
(45) Date of Patent: Jul. 14, 2026

(54) SYSTEMS, METHODS, AND APPARATUS FOR MODELING AND OPTIMIZING DIALYSIS EFFECTS

(71) Applicant: INNCELEREX, Jersey City, NJ (US)

(72) Inventor: Parviz Ghahramani, Weehawken, NJ (US)

(73) Assignee: INNCELEREX, Jersey City, NJ (US)

( * ) Notice: Subject to any disclaimer, the term of this patent is extended or adjusted under 35 U.S.C. 154(b) by 345 days.

(21) Appl. No.: 18/330,780

(22) Filed: Jun. 7, 2023

(65) Prior Publication Data

US 2023/0390467 A1 Dec. 7, 2023

Related U.S. Application Data

(60) Provisional application No. 63/349,728, filed on Jun. 7, 2022.

(51) Int. Cl.
| | |
|---|---|
| *A61M 1/16* | (2006.01) |
| *G09B 23/28* | (2006.01) |
| *G16H 20/10* | (2018.01) |

(52) U.S. Cl.
CPC ........ *A61M 1/1613* (2014.02); *A61M 1/1621* (2014.02); *G09B 23/28* (2013.01); *G16H 20/10* (2018.01); *A61M 2205/50* (2013.01)

(58) Field of Classification Search
None
See application file for complete search history.

(56) References Cited

U.S. PATENT DOCUMENTS

| | | | | | |
|---|---|---|---|---|---|
| 6,733,471 | B1 * | 5/2004 | Ericson | ............... | A61M 1/3672 |
| | | | | | 210/348 |
| 2005/0284815 | A1 * | 12/2005 | Sparks | ................. | G01F 1/8445 |
| | | | | | 604/4.01 |
| 2011/0163030 | A1 * | 7/2011 | Weaver | ................. | G01F 23/296 |
| | | | | | 210/120 |
| 2014/0099617 | A1 * | 4/2014 | Tallman, Jr. | ......... | G09B 23/303 |
| | | | | | 434/262 |
| 2016/0180053 | A1 * | 6/2016 | Fuertinger | ............. | G16H 20/10 |

\* cited by examiner

*Primary Examiner* — Jonathan M Peo
(74) *Attorney, Agent, or Firm* — RAPHAEL BELLUM PLLC

(57) ABSTRACT

Systems, methods, and devices model, identify, and predict effects of dialysis on drugs and chemical substances in patients. The systems estimate and determine effects of dialysis on elutes and drugs and solve problems with prior systems in determining effects of dialysis on drugs and dosages, especially the removal of target substances from the blood of patients during dialysis. Drug and medicine dosage adjustments for patients undergoing dialysis are made by considering the dialysis systems, patients, and drug variables and the extent to which they affect drug removal. Patients receive proper dosing by accounting for the effects of their dialysis. Systems and methods include a combination of ex vivo simulated treatments and in-silico modeling and simulation. The effects of dialysis are estimated and determined for various drugs and dosages. A reliable and effective surrogate for performing studies on patients provides guidance for use of the drugs in dialysis patients.

3 Claims, 15 Drawing Sheets

System (100)

Ex-vivo Experiment - High Level Algorithm and Schematic of Cybernetic Dialysis™ and Its Use

CRRT: continuous renal replacement therapy. Most common types of CRRT include continuous venovenous hemofiltration (CVVH), continuous venovenous hemodialysis (CVVHD), and continuous venovenous hemodiafiltration (CVVHDF)
IHD: Intermittent hemodialysis

Figures 3, 3B:
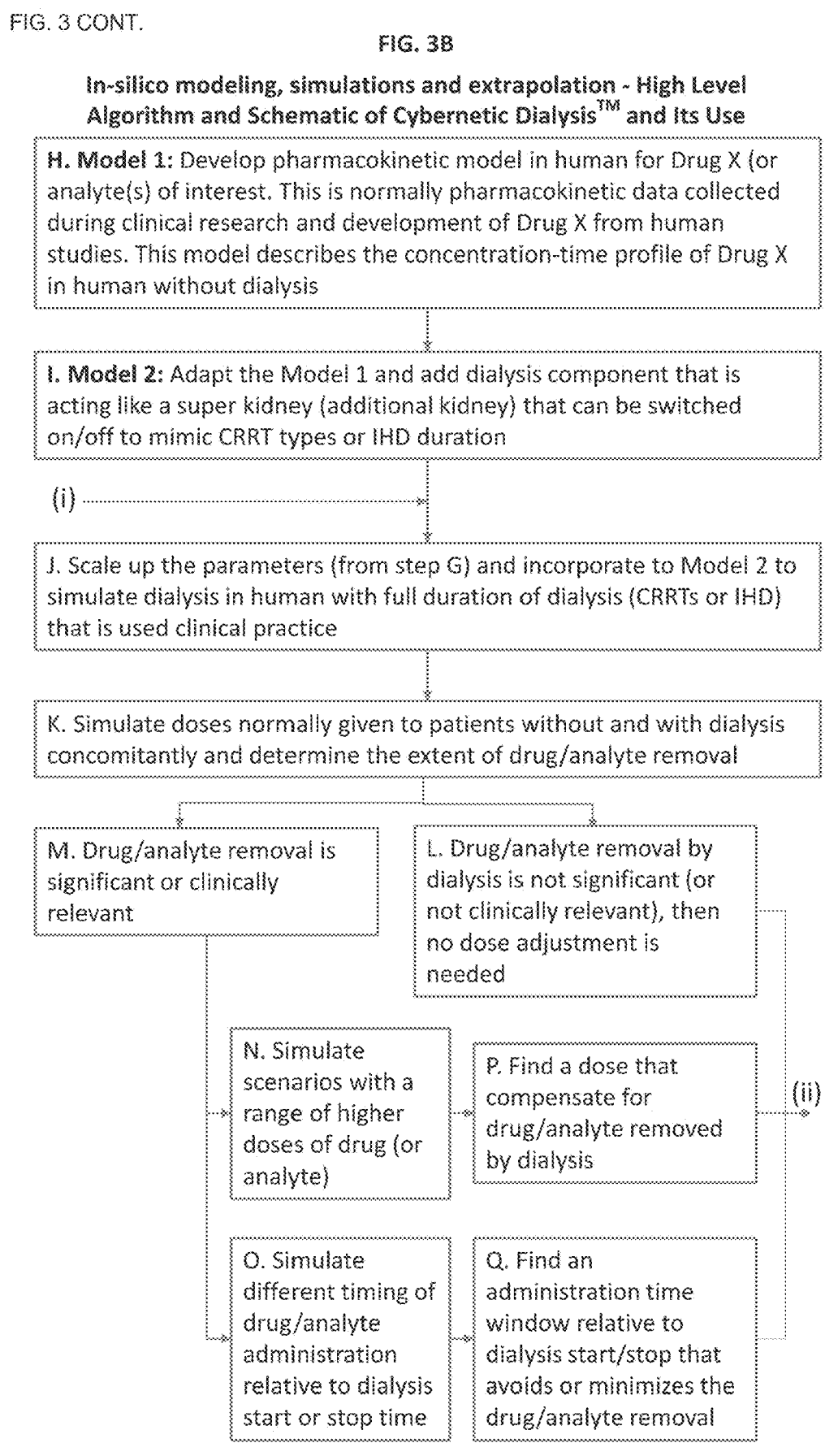

In-silico modeling, simulations and extrapolation - High Level Algorithm and Schematic of Cybernetic Dialysis™ and Its Use

H. Model 1: Develop pharmacokinetic model in human for Drug X (or analyte(s) of interest. This is normally pharmacokinetic data collected during clinical research and development of Drug X from human studies. This model describes the concentration-time profile of Drug X in human without dialysis

I. Model 2: Adapt the Model 1 and add dialysis component that is acting like a super kidney (additional kidney) that can be switched on/off to mimic CRRT types or IHD duration (i)

J. Scale up the parameters (from step G) and incorporate to Model 2 to simulate dialysis in human with full duration of dialysis (CRRTs or IHD) that is used clinical practice K. Simulate doses normally given to patients without and with dialysis concomitantly and determine the extent of drug/analyte removal M. Drug/analyte removal is significant or clinically relevant L. Drug/analyte removal by dialysis is not significant (or not clinically relevant), then no dose adjustment is needed N. Simulate scenarios with a range of higher doses of drug (or analyte)

P. Find a dose that compensate for drug/analyte removed by dialysis (ii)

O. Simulate different timing of drug/analyte administration relative to dialysis start or stop time Q. Find an administration time window relative to dialysis start/stop that avoids or minimizes the drug/analyte removal

Figures 3, 3C:
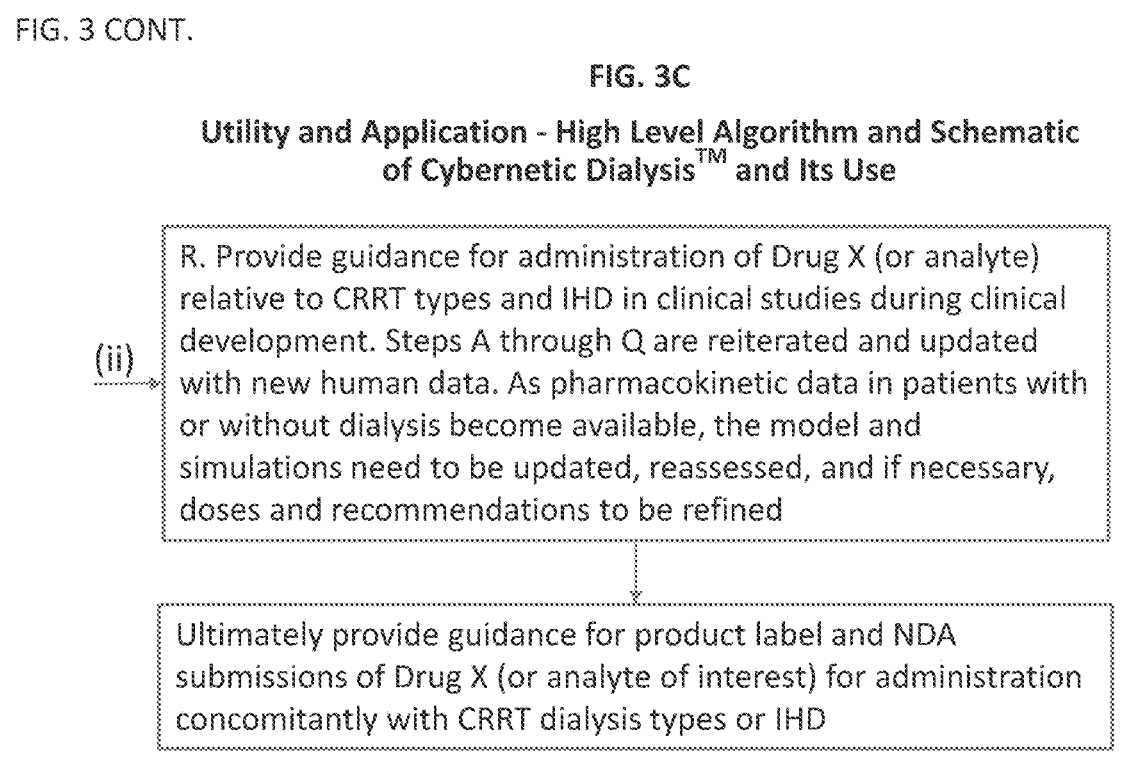

**Utility and Application - High Level Algorithm and Schematic
of Cybernetic Dialysis™ and Its Use**

(ii)

R. Provide guidance for administration of Drug X (or analyte)
relative to CRRT types and IHD in clinical studies during clinical
development. Steps A through Q are reiterated and updated
with new human data. As pharmacokinetic data in patients with
or without dialysis become available, the model and
simulations need to be updated, reassessed, and if necessary,
doses and recommendations to be refined Ultimately provide guidance for product label and NDA
submissions of Drug X (or analyte of interest) for administration
concomitantly with CRRT dialysis types or IHD 1350, 1350A, 1360

SYSTEMS, METHODS, AND APPARATUS FOR MODELING AND OPTIMIZING DIALYSIS EFFECTS

CROSS-REFERENCE TO RELATED APPLICATION

This application claims benefit of priority from U.S. Provisional Application No. 63/349,728 filed on Jun. 7, 2022, the entire contents of which are incorporated by reference in this application.

TECHNICAL FIELD

The systems and methods in accordance with the invention include apparatus and processes for modeling removal of target substances from the blood of patients during dialysis treatments. More particularly, the systems and methods of the invention include processes for modeling, determining, and optimizing the effect of dialysis for elutes, drugs of interest, particular patients, target compounds, treatment regimens, and the like.

BACKGROUND

Medicines are given in precise amounts to patients to achieve desired efficacy. During development of a new medicine, the dose and drug concentrations are fine tuned to arrive at precise dose(s) that produce specific concentration range(s) in blood (or an amount in the body).

Clinical trials are conducted to collect data and other information regarding the safety and efficacy of drugs and medical devices. There are several steps and stages of approval in the clinical trials process before a drug or device can be sold in the consumer market. These steps typically require millions of dollars of investment and take years to complete. In a clinical setting, drug patients may undergo dialysis while also receiving the drug.

Dialysis is designed to remove small molecules that are body waste products, such as urea and creatinine. But, because the patient's whole blood is cycled through dialysis, the process often removes the drug from the body along with the waste material. The extent of this unwanted drug removal varies from medicine to medicine and by dialysis types. So, dialysis introduces an uncertainty in the amount of medicine left in the body and the concentration of the medicine in the blood. This may lead to under exposure and lack of efficacy. If a physician wants to dose more of the medicine to compensate for the effect of dialysis, they will need a precise estimate of the amount or concentration of the drug that is removed from the body and the amount or concentration of the drug that needs to be replenished. This estimate depends on many factors such as the type of dialysis, the type of filters and machines used, the nature of the medicine, the machine settings for dialysis, the duration of dialysis, the types of replacement solutions used in dialysis, and many other factors. In theory, these conditions can be tested during drug research and development to make dosing recommendations in clinical studies. But in practice, it is not practical and often not possible to collect this data adequately, because there are many permutations of conditions and factors that form subgroups of dialysis. Each subgroup requires a sizeable number of patients (e.g., 6-12) to collect meaningful and conclusive data to guide dosing in patients undergoing dialysis. Doing dialysis studies within clinical trial programs in research and development of a medicine is a burden, including cost, time, labor, and feasibility, and is hampered by practical considerations. Therefore, for a vast majority of drugs, dialysis studies within clinical trial programs are not performed or fulfilled. Drugs are developed and are on the market with little or no information as to how a physician can properly dose in dialysis to achieve optimal efficacy and to avoid toxicity.

Conducting additional phases of a clinical trial to test a new drug in a dialysis study presents many challenges to investigators. Some challenges include the time and financial demands of clinical trials, the complexity of FDA regulations, inadequate research training among many clinicians, pressures to which both investigators and volunteers are subjected during the course of a trial, and data collection challenges (e.g., medical records, quality control, etc.). Therefore, there is a need for reliable, cost-effective predictive models for performing a clinical trial, in silico, to supplement and/or replace actual clinical trials.

SUMMARY

Systems, methods, and devices in accordance with the invention model, identify, and predict the effects of dialysis on drugs, medications, and chemical substances in patients. Systems, methods, and devices in accordance with the invention are configured for determining and estimating the effect of dialysis on elutes and drugs of interest and for solving problems with prior systems and methods in determining effects of dialysis on many drugs and dosages.

These embodiments provide a technical solution to a technical problem. One technical problem being solved is the inability to make drug and medicine dosage adjustments for patients undergoing dialysis. The technical problem manifests as difficulties identifying and predicting the effects of dialysis on drugs, medications, and chemical substances in patients. In practice, this is problematic because dialysis patients are subject to extracorporeal clearance of small molecules, including many drugs. The extent to which dialysis removes a particular drug from plasma is dependent upon a number of factors, including water solubility, molecular weight, protein binding, and volume of distribution, for example. Patients can be over- or under-dosed when the effects of their dialysis, including drug metabolism and transport, are not properly accounted for.

In the prior art, there was no way to accurately and effectively account for dialysis systems and the manner and extent to which they removed drugs and other medicines from patients undergoing dialysis. Prior systems tracked the amount of the drug or the medicine in the patients' blood, but the measurements were done after the fact and provided wildly varying outcomes. With prior systems and techniques, there was no way to ensure patients received the proper dosage of the drug when taking into account the dialysis treatments.

Moreover, the prior art relies on subjective decisions and experiences of individual clinicians, which leads to wildly varying outcomes from instance to instance. Thus, prior art techniques did little if anything to address removal of molecules in dialysis procedures influenced by flow rates of the dialysis solution and the patient's blood; the surface area, pore size, and "geometry" of the filter; and the technique used.

Cybernetic Dialysis™ systems and methods in accordance with the invention include a combination of ex vivo simulated treatments and in-silico modeling and simulation. The systems, methods, and devices of the invention determine and estimate the effect of dialysis on elutes and drugs of interest and solve problems with prior systems and methods in determining effects of dialysis on many drugs and dosages. The Cybernetic Dialysis™ systems, devices, and methods in accordance with the invention provide a reliable and effective surrogate for performing studies on patients. Due to many practical hurdles, including those outlined above, drugs are developed, approved, and marketed without sufficient guidance regarding use of the drug in dialysis patients. As a consequence, dialysis patients are often denied optimal treatment or are at risk of under-dosing or over-dosing when they receive the drugs. The systems, devices, and methods of the invention provide reliable and accurate results to predict optimal drug treatment for dialysis patients.

The devices, methods, and computer systems in accordance with the invention generate one or more virtual patients in silico. The one or more virtual patients can be used, for example, to conduct a virtual clinical trial (e.g., to determine safety and efficacy of a therapy, such as dialysis and its effect on drug dosage and efficacy). The virtual patients can mathematically represent one or more physiological systems in an actual patient. As further in detail below, the virtual patients can be used, for example, to assess the effect of a therapy, to optimize a therapy for administration to actual patients, and to reject a therapy based on observed adverse effects on virtual patients, etc.

The systems, devices, and methods in accordance with the invention include an integrated Cybernetic Dialysis™ approach including collecting data from a population of plasma (or blood) including an analyte or spiked with a drug of interest. The population of plasma or blood samples are subject to conditions that mimic dialysis conditions varying in type of dialysis, filters, dialysate or replacement solutions, anticoagulant type, rate, and set up. The simulated plasma or blood therapies generate data for characterizing the effect of dialysis conditions on a drug or medicine. These methods are performed to identify and characterize the relationship between an amount or rate of drug removal and a type of filter and a rate of flows (e.g., blood, dialysate, replacement fluid, etc.), and other numerous dialysis conditions. The plasma and blood simulated treatment therapies are done at the extremes of each condition. For example, one plasma or blood therapy can be performed with a high permeability filter and another with a low permeability filter, or one treatment can be made with a low medicine concentration and another with a high medicine concentration, or high and low flows of blood or fluid. By performing the simulated treatments at both ends of the respective spectra, a complete range of variables and effects can be accounted for.

The data collected from the simulated (dialysis) treatments of the population of plasma or blood is used in generating in silico one or more virtual patients. The virtual patients are generated in silico by mathematical models developed to more closely mimic dialysis conditions in a patient. For example, the amount or concentration of a drug removed is scaled by normal duration of dialysis applied in clinical practice, by volume of blood, by total fluid in a patient, by a specific configuration of filter, by flow rates, and/or by type of dialysis. The in silico models utilize the simulated plasma or blood treatment therapy data described above to scale and to interpolate (or extrapolate) to all conditions between the extremes and also to mimic dialysis configurations that are not necessarily tested in the simulated plasma or blood therapies.

The systems and methods in accordance with the invention enable accurate prediction of dialysis effects on a drug in early stages of research and development and reduce cost, time, and the number of studies needed to estimate a dialysis effect on a drug or other medicine. Consequently, the systems and methods in accordance with the invention allow dialysis effects to be characterized in early stages of medicine research and development paving the way to allow real patients with dialysis to be included in the clinical studies in the course of drug development, rather than in ad hoc research after drug approval (if at all). Consequentially, the Cybernetic Dialysis systems, devices, and methods in accordance with the invention provide a more feasible approach early in the development process and enable many drug approvals and registrations with regulatory authorities to include approval for patients on dialysis. This expands the patient base eligible for administration of the medicine. The invention can also be used for medicines that are approved or are on the market that often have little or no guidance or information regarding administration in dialysis patients.

BRIEF DESCRIPTION OF THE DRAWINGS

FIGS. 3A-3C show an exemplary implementation of a Cybernetic Dialysis modeling algorithm to predict and extrapolate dialysis effects in accordance with the invention.

DETAILED DESCRIPTION

Simulated Treatment Configuration

Figure 1:
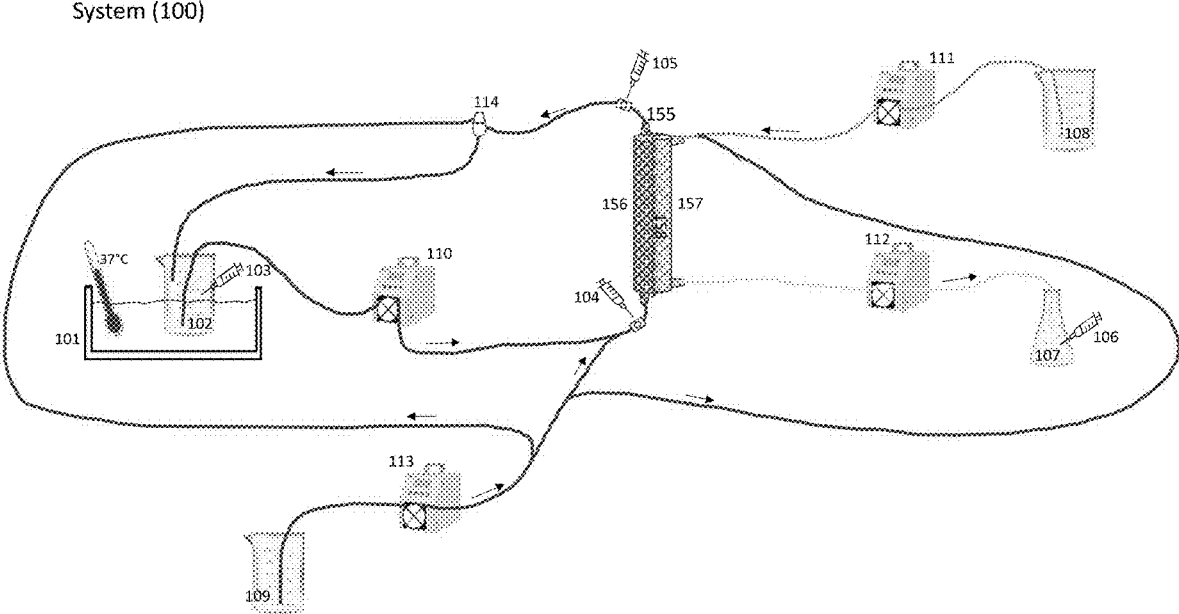
FIG. 1 shows an exemplary system configured to conduct simulated treatments in accordance with the invention to test a drug or analyte.

FIG. 1 illustrates an exemplary system 100 and configuration for a simulated treatment on a drug or analyte of interest. The exemplary system 100 of FIG. 1 was designed and built to mimic Continuous Renal Replacement Therapy (CRRT). CRRT is a method of slower, continuous dialysis to allow solute and fluid homeostasis. CRRT includes intermittent hemodialysis and peritoneal dialysis. It is typically performed through pump-driven venovenous extracorporeal circuits and acts as renal support through blood purification to allow solute and fluid homeostasis. CRRT is often chosen for renal replacement in hemodynamically unstable patients, and it is often employed in the intensive care unit. With a slower rate of fluid removal, CRRT theoretically causes less hypotension than other dialysis techniques. Another advantage of CRRT for these patients is that they often require a large volume of fluid administration, including medications and parenteral nutrition, and CRRT can prevent an overloaded state.

With some modification, the exemplary system 100 configuration in FIG. 1 also mimics Intermittent Hemodialysis (IHD). IHD is a more traditional type of dialysis that is still widely used and is highly effective in achieving solute removal by solute clearance and fluid removal by ultrafiltration. In contrast to the slower rate of fluid removal, IHD achieves solute removal by solute clearance and fluid removal over a short period of time, typically 3-5 hours. Depending on the type of dialysis simulated, some of the components shown in FIG. 1 may not be used. For example, in some embodiments simulating some types of CRRT, if a dialysate reservoir 108 and a peristaltic pump dialysate are used, then a replacement fluid reservoir 109 and a peristaltic pump effluent 113 are not used, and vice versa.

FIG. 1 shows an exemplary embodiment where bovine plasma or blood containing the analyte (e.g., spiked with a drug) is pumped through a system 100 and passed through a filter 155 that has two chambers (blood side chamber 156 and dialysate side chamber 157) separated by a membrane 158. The blood or plasma is introduced to the blood side 156 of the filter. Dialysate fluid that has no drug (nor analyte of interest) is pumped through the other side 157 of the filter. This process creates a movement of the analyte of interest from the blood side 156 of the filter to the dialysate side 157 and ultimately excretion into an effluent container 107 (simulating drug removal). The pumps 110, 111, 112, 113 are set at typical clinical levels (e.g., 300-500 mL/min) for pump speed and are optimized based on performance criteria (and by trial and error) for the specific treatment simulation.

In some embodiments, the system 100 is run for 1 hour, and during this time samples (500 µL each) are taken at the respective sample points 103, 104, 105, 106 at time 0, 10, 20, 30, 40 and 60 minutes after starting the pumps 110, 111, 112, 113. These samples are assayed for the analyte of interest. These are the numerical treatment simulation results that are used in silico (described below) to scale and to predict human dialysis situations (i.e., create a virtual patient) and also to extend the predictions to many other dialysis settings (e.g., different filter types, flow rates, type of fluids pumped in, etc.) that are used in different clinical conditions.

Virtual Patient

In the Cybernetic Dialysis™ methods, devices, and systems in accordance with the invention, the results of the concentration of analyte (obtained from assay) in the simulated treatments are used to estimate an amount and a rate of analyte/medicine removal from plasma in the experiment, and these results are scaled to virtual patients with physiological values for blood volume and body fluid volume, and are also interpolated or extrapolated to other types of filters, flow rates, and dialysis types.

The Cybernetic Dialysis™ systems, devices, and methods in accordance with the invention create virtual patients to account for the effects of dialysis on medicines and analytes. The Cybernetic Dialysis systems, devices, and methods in accordance with the invention incorporate many methods and configurations for performing dialysis in clinical practice. These include the two primary families of dialysis by filter, namely CRRT and IHD, as outlined above. Additionally, the invention accounts for polyacrylonitrile, polymethylmethacrylate, polysulfone, polycarbonate, polyethylene, polyamide, and other filter types for each dialysis family. Systems, devices, and methods in accordance with the invention create virtual patients based on different flow rates and duration of dialysis, including type of vascular access, filter type, device used, and dose and rout of erythropoietin stimulation agents used as well as different dilution methods (e.g., pre- or post-blood). Likewise, the systems, devices, and methods in accordance with the invention can be configured to simulate different types of dialysates (or replacement) fluid, including high-molecular-weight agents such as glucose polymer-containing solutions (e.g., icodextrin), polypeptides, and dextrans, as well as low-molecular-weight agents such as glucose-containing solutions, amino acid-containing solutions, Xylitol-containing solutions, glycerol-containing solutions, and other dialysate solutions. Also, the systems, devices, and methods in accordance with the invention can be configured to simulate different types of anticoagulants (e.g., citrate, heparin, and the like) as well as different concentrations (e.g., high and low) of the analyte.

Even with this limited list of configurations, there are 2304 different permutations of the elements used in dialysis. This alone makes it very difficult to investigate all these conditions and has contributed to the dearth of systems to create virtual patients. The Cybernetic Dialysis™ systems, devices, and methods in accordance with the invention account for the extremes of a given condition, and by doing so are able to limit the number and type of elements and configurations used to create virtual patients. In silico methods are then applied to interpolate or extrapolate to additional treatment configurations between the extremes.

In-Silico Methods

The blood concentration-time course of medicine is routinely characterized during the course of drug development. The blood concentration-time course is often described and summarized by mathematical models that are published or by a variation of those models. These existing models represent rates of absorption as well as distribution and elimination of a drug in the body where elimination may be by liver or by kidney. The in-silico methods used in accordance with the Cybernetic Dialysis™ invention utilize similar base models but add a dialysis component that is turned on for a period of time to represent dialysis. The rate of drug removal by this dialysis component is informed by the rates and concentration data collected from the simulated treatment stage of the invention described above.

In one example implementation of the Cybernetic Dialysis™ invention, a mathematical model is implemented in R (software). The model algorithms are coded and then used to predict and extrapolate dialysis in humans with conditions used in the clinical practice. One example modeling algorithm to predict and extrapolate dialysis in accordance with the invention is shown in FIGS. 3A-3C.

Figure 3A:
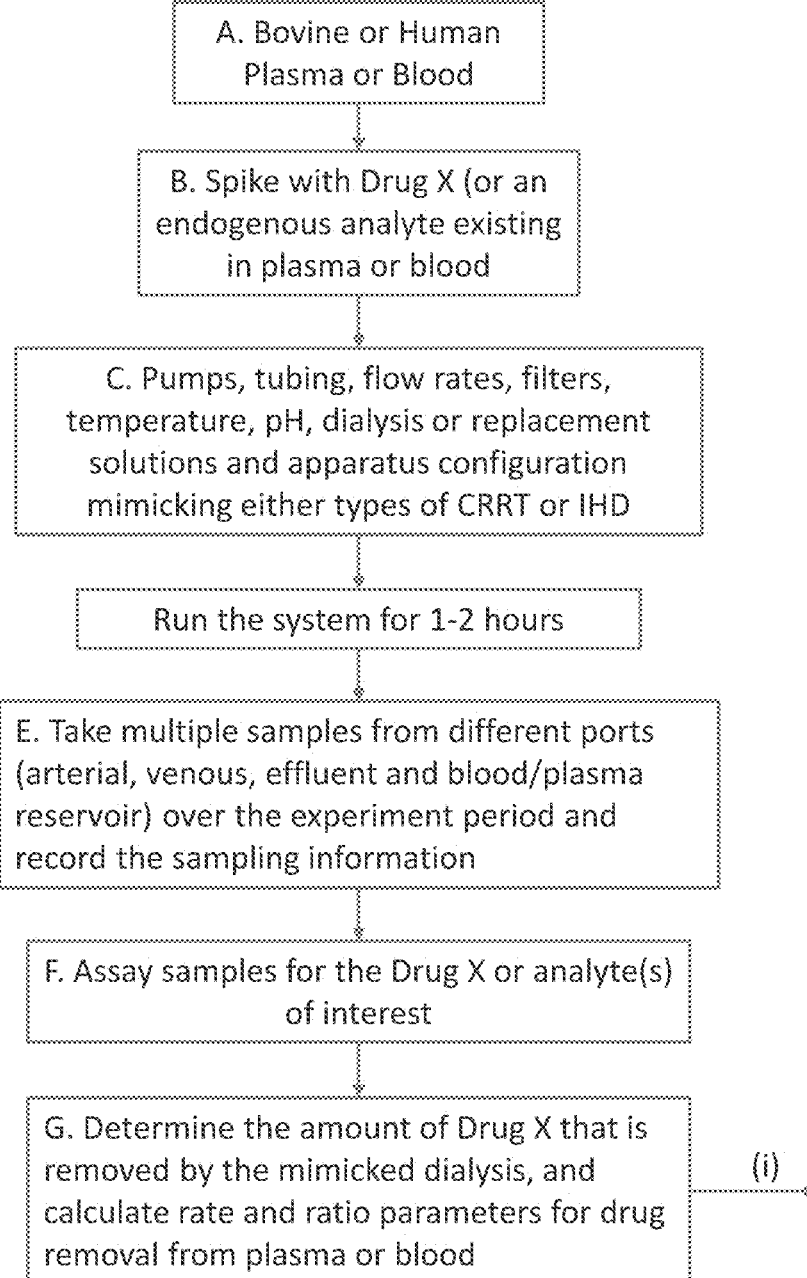

As shown in an exemplary algorithm and schematic of the invention in FIGS. 3A-3C, the treatment simulation and in-silico modeling, simulations, and extrapolation are used to determine the effects of dialysis on a drug or analyte of interest. In blocks A and B of FIG. 3A, bovine or human plasma or blood is spiked with a drug or an exogenous analyte existing in plasma or blood. In block C, pumps, tubing, flow rates, filters, temperature, pH, dialysis or replacement solutions and apparatus are configured to mimic a type of CRRT (Continuous Renal Replacement Therapy) or IHD (Intermittent Hemodialysis). In block D, the system is run for approximately 1-2 hours. In block E, multiple samples from different ports 103, 104, 105, 106 (arterial, venous, effluent, and blood/plasma reservoir) are taken during the treatment simulation and the sampling information is recorded. In block F, the samples for the drug/analyte collected are assayed. In block G, the amount of the drug that is removed by the treatment simulation is determined, and rate and ratio parameters for the drug removal from plasma or blood are calculated.

Referring to FIG. 3B, in block H, the in-silico modeling, simulations, and extrapolation are performed to create a virtual patient that can be used to predict and determine the effects of dialysis on the drugs/analytes. Specifically, pharmacokinetic model in a human for the drug is developed by using the collected pharmacokinetic data from clinical research and development human trials. This modeled pharmacokinetic model describes the concentration-time profile of the drug in humans without dialysis. In block I, the model is adapted, and dialysis components are added. The dialysis component acts like a(n additional) kidney that can be switched on and off to mimic CRRT types or IHD duration.

In block J, the parameters from block G are scaled up and incorporated into the adapted model from block I. This simulates dialysis in humans with the full duration of dialysis (CRRTs or IHD) that is used in clinical practice. In block K, normal doses that are given to patients without dialysis and with dialysis are simulated concomitantly and the extent of drug/analyte removal is determined. If the drug/analyte removal by dialysis is not significant (i.e., clinically relevant), no dose adjustment is needed in block L, and the process continues to block R where guidance is provided for administration of the drug/analyte relative to CRRT types and IHD in clinical studies during clinical development. Blocks A-Q are reiterated and updated with new human data. As pharmacokinetic data in patients with or without dialysis become available, the model and simulations can be updated, reassessed, and if necessary, doses and recommendations can be refined. Ultimately guidance is provided for product labels and NDA submissions of the drug/analyte for administration concomitantly with CRRT dialysis types or IHD.

If, however, after block K, the drug or analyte removal is significant (i.e., clinically relevant), the process follows block M to block N where scenarios are simulated with a range of higher doses of the drug. The process then moves to block P, where a dose is identified that compensates for the drug/analyte removal by dialysis. Simultaneous to block N, in block O, different timing of the drug/analyte administration relative to dialysis start/stop times is simulated and in block Q, an administration time window relative to dialysis start/stop times is determined that avoids or minimizes the drug/analyte removal. When the activities in blocks P and Q are complete, the process continues to block R illustrated in FIG. 3C as described above.

The dialysis effect on drug removal is predicted for different configurations of dialysis and their effects, and a virtual patient is created. Then, the models are interrogated for different conditions of interest. For example, a drug researcher may be interested in the effect of a particular dialysis type or configuration on a particular drug and receive guidance on dosing the drug to patients. The models created by the systems and methods in accordance with the Cybernetic Dialysis™ invention provide such capabilities and guidance.

Figure 2:
FIG. 2 shows an exemplary embodiment of a Cybernetic Dialysis™ system in accordance with the invention.

One example implementation of a Cybernetic Dialysis system in accordance with the invention is shown in FIG. 2. FIG. 2 shows an exemplary system 200 used to run a study that had two analytes of interest. One analyte was creatinine used as control, and the other was drug X (a drug under development). The Cybernetic Dialysis™ system 200 measures how much of drug X and how much creatinine is removed by dialysis and (referring back to FIG. 1) includes water bath 101 with shaking tray with thermal control set at 37° C. (101), and a beaker 102 containing plasma or blood with the analyte of interest (for example, spiked with known amount of medicine X. The sampling point from plasma or blood 103, a sampling point from plasma or blood prior to filter 104, a sampling point from plasma or blood post filter 105, a sampling point from effluent fluid 106, an effluent collection container 107, a dialysate reservoir container 108, a replacement fluid reservoir 109, a peristaltic pump for plasma or blood 110, a peristaltic pump for dialysate 111, a peristaltic pump for effluent 112, and a peristaltic pump for effluent 113 are also shown. Additionally, a deaeration chamber 114 is also shown as well as the filter 155 with blood side chamber 156 and dialysate side chamber 157. As outlined above, the exemplary configuration shown in FIGS. 1 and 2 can be modified depending upon the drug being evaluated and the dialysis configuration assessed.

Experimental Results and Application of Ex-Vivo Experiment Treatment Simulations Removal of creatinine in bovine plasma is used in some example embodiments of the invention to demonstrate the systems, methods, and devices in accordance with Cybernetic Dialysis™. Creatinine represents a traceable endogenous analyte, a drug, or an exogenous analyte.

As shown in FIG. 1, methods in accordance with the Cybernetic Dialysis™ invention were applied to bovine plasma containing creatinine, and samples were taken at several points (including at a sampling point from plasma or blood 103, a sampling point from plasma or blood prior to filter 104, a sampling point from a sampling point from plasma or blood post filter 105, and from a sampling point from effluent fluid 106) up to 60 minutes after start of ex-vivo dialysis. The treatment simulation was replicated with two membrane types (M150 AN69 and HF1400) that represent a spectrum of membranes.

The M150 AN69 membrane provides continuous fluid management and renal replacement therapy. The M150 AN69 membrane is typically used for patients who have acute renal failure, fluid overload, or both. The M150 AN69 membrane is used in veno-venous therapies, including SCUF (slow continuous ultra-filtration), CVVH (Continuous Veno-Venous Hemofiltration), CVVHD (Continuous Veno-Venous Hemodialysis), and CVVHDF (continuous venovenous hemodiafiltration).

The HF1400 membrane is a polyarylethysulfone (PAES) membrane and can be used to perform all CRRT therapies (SCUF, CVVH, CVVHD and CVVHDF). The HF1400 membrane is designed with a neutral charge to enhance ultrafiltration of solutes with minimal protein adsorption.

Table 1 Table 1 shows creatinine concentrations for each of the membranes at sampling time points over one hour. For both membranes, there was appreciable removal of creatinine from plasma over time. The creatinine removal from the bovine plasma was largest at 60 min post start of dialysis. Starting creatinine concentration at time zero (prior to starting the ex-vivo portion of a Cybernetic Dialysis™ method in accordance with the invention) was 8.366 and 8.581 µg/mL for the AN69 M150 and for the HF1400 membranes, respectively. By the end of the treatment simulation (at 60 minutes), there was a 60% and a 56% reduction in creatinine on the arterial side of the AN69 M150 and the HF1400 membrane, respectively. There was a 66% and a 63% reduction in creatinine on the venous side of the M150 AN69 and the HF1400 membrane, respectively. This represents a significant reduction in creatinine amount (concentration) in the system over time.

Figure 4:
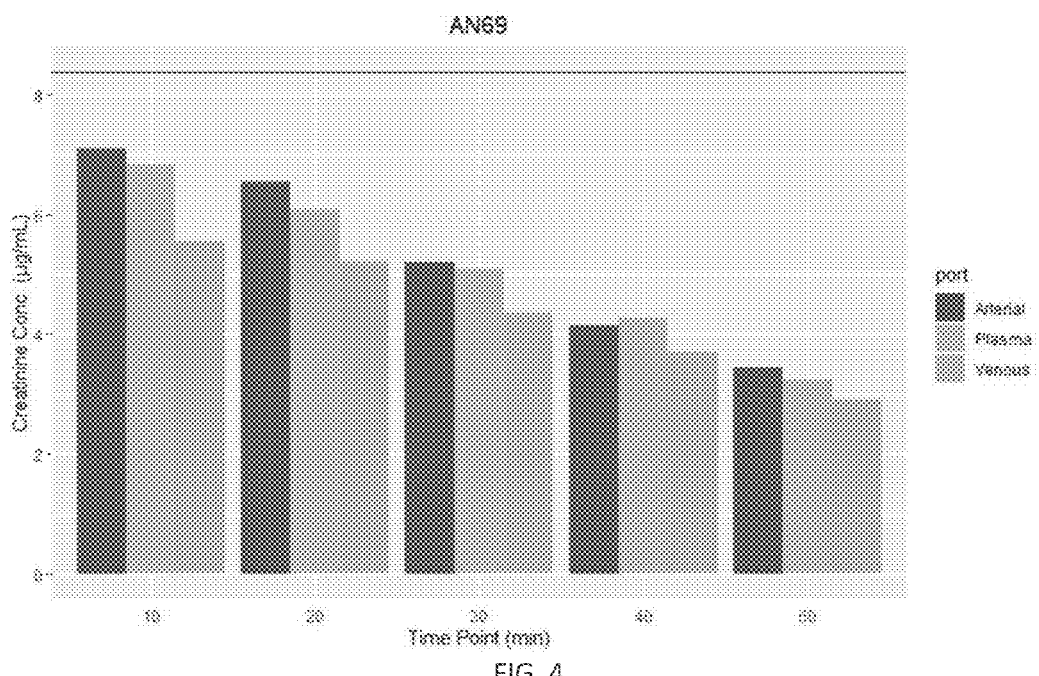
FIG. 4 shows example arterial, venous, and plasma reservoir concentrations of creatinine for an M150 AN69 membrane in accordance with the invention and indicative of a steady reduction in the concentration of creatinine over time.
Figure 5:
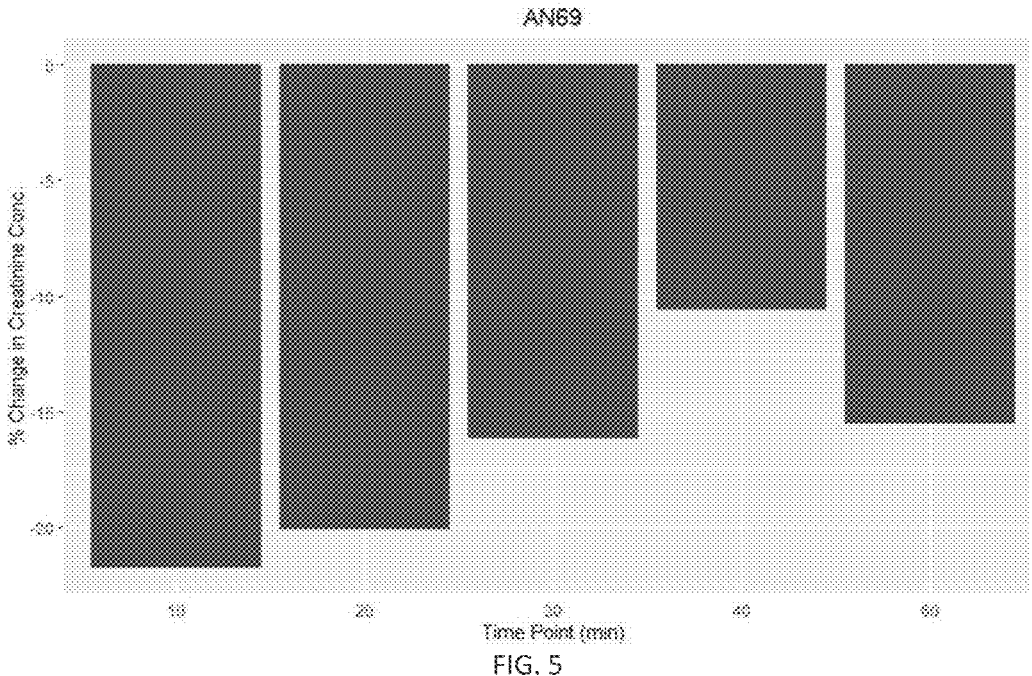
FIG. 5 shows a percentage change in creatinine concentration on a venous side vs. an arterial side of an M150 AN69 membrane (at each timepoint) in an exemplary embodiment of the invention.

FIG. 4 shows arterial, venous, and plasma reservoir concentrations of creatinine for M150 AN69 membrane taken at the indicated ports that indicates a steady reduction in the concentration of creatinine over time. The solid horizontal black line at the top of the graph is the concentration of creatinine in plasma reservoir at time zero (i.e., prior to starting dialysis). FIG. 4 also shows venous concentrations of creatinine are consistently lower than the arterial concentration with a mean of −16.83 µg/mL (range −21.77 to −10.59) as shown in FIG. 5. That is, FIG. 5 shows a percentage change in creatinine concentration on a venous side vs. an arterial side of an M150 AN69 membrane (at each timepoint) in an exemplary embodiment in accordance with the invention. These results support the conclusion that the membrane and the system remove creatinine continuously at each cycle of plasma through the membrane.

Figure 6:
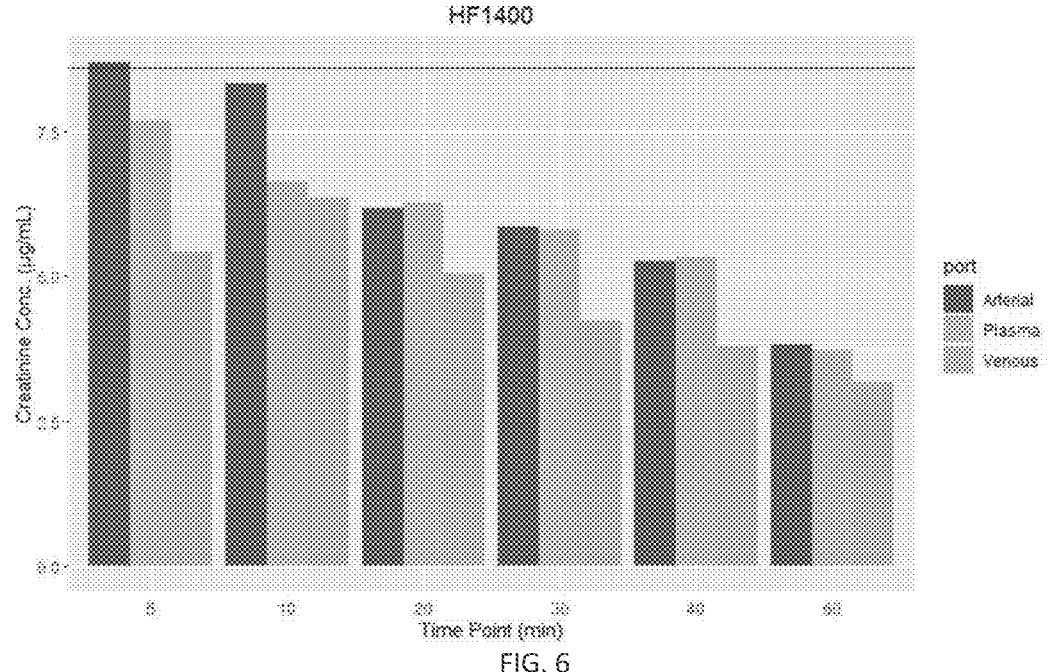
FIG. 6 shows creatinine concentrations over time at the arterial and venous sides of membrane HF1400 and in the plasma reservoir in an exemplary embodiment of the invention.
Figure 7:
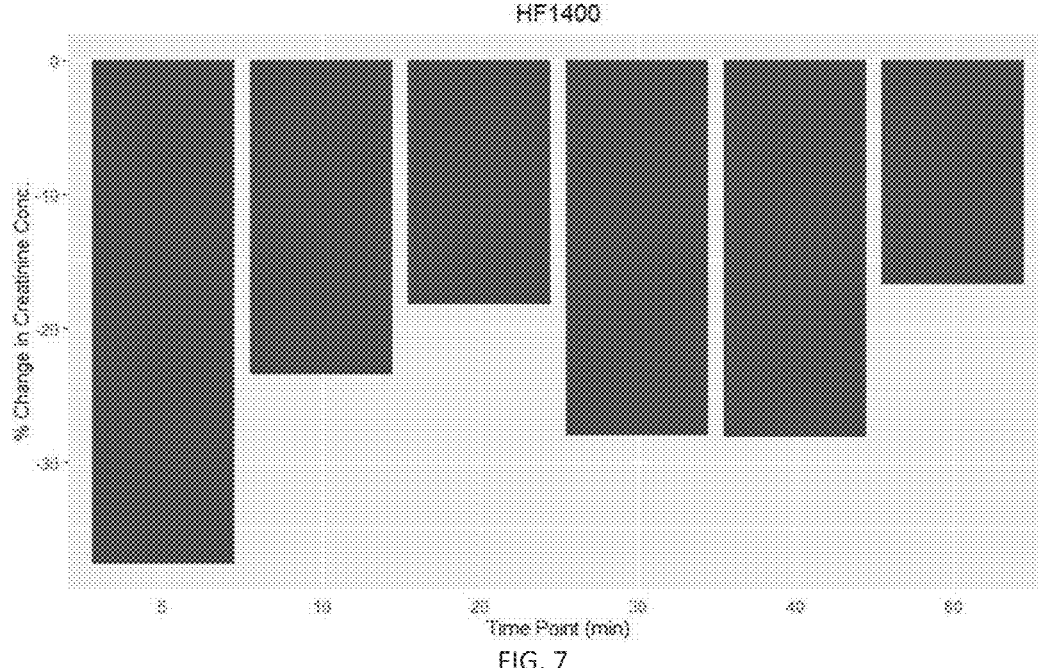
FIG. 7 shows percentage changes in creatinine concentration on a venous side vs. an arterial side of an HF1400 membrane (at each timepoint) in an exemplary embodiment of the invention.

FIG. 6 shows creatinine concentrations over time at the arterial and venous sides of membrane HF1400 and in the plasma reservoir in an exemplary embodiment in accordance with the invention. The plasma reservoir concentrations of creatinine for an HF1400 membrane indicate a steady reduction in concentration of creatinine over time. In FIG. 6, the solid horizontal black line is the concentration of creatinine in the plasma reservoir at time point zero (i.e., prior to starting dialysis). FIG. 6 also shows the venous concentration of creatinine is consistently lower at each timepoint (and port) than the arterial concentration with a mean of −25.37 µg/mL (range −37.64 to −16.75) See FIG. 7. These results support the conclusion that the membrane and system remove creatinine continuously at each cycle of plasma through the membrane.

Figure 8:
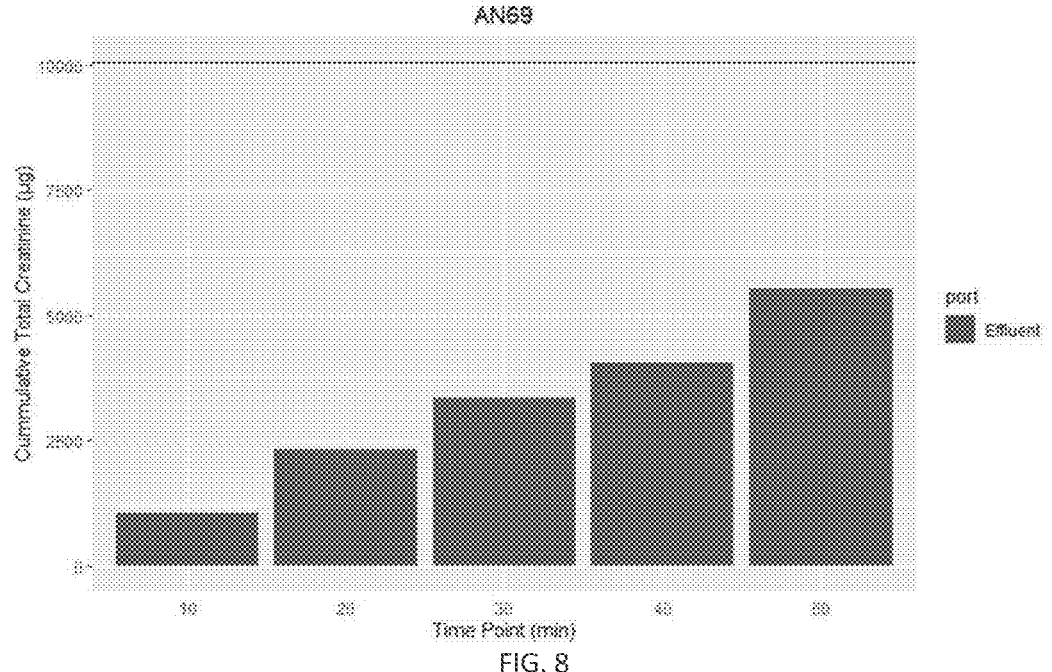
FIG. 8 shows a cumulative amount of creatinine removed from plasma for an M150 AN69 membrane that was collected in effluent in an exemplary embodiment of the invention.

FIG. 8 shows a cumulative amount of creatinine removed from plasma for an M150 AN69 membrane that was collected in effluent in an exemplary embodiment in accordance with the invention. In a treatment simulation with an M150 AN69 membrane, FIG. 8 shows the total amount of creatinine removed (that ends up in effluent) continuously increased over the period of dialysis. At the end of the dialysis period (at 60 minutes), the total amount of creatinine in the effluent was 68.0% of total amount of creatinine in the reservoir at time zero.

Figure 9:
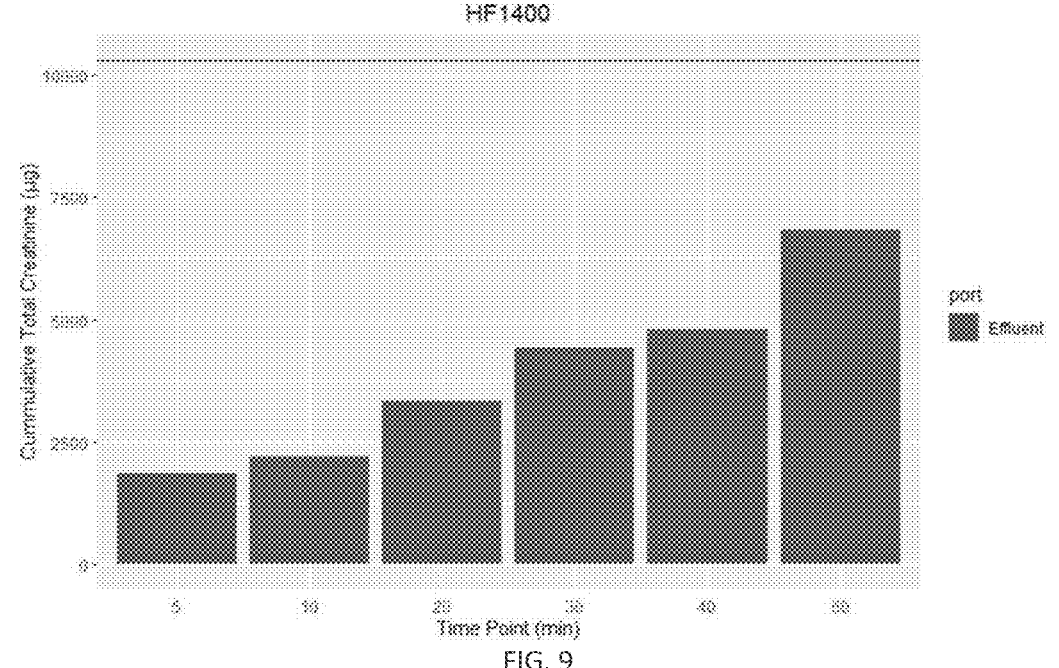
FIG. 9 shows a cumulative amount of creatinine removed from plasma for an HF1400 membrane that was collected in effluent in an exemplary embodiment of the invention.

FIG. 9 shows simulated treatment results with an HF1400 membrane where the cumulative amount of creatinine removed from plasma (and ending up in effluent) continuously increased over the period of dialysis. The solid horizontal black line is the total amount of creatinine in the plasma reservoir at time zero (i.e., prior to starting dialysis). At the end of dialysis period (at 60 minutes), the total amount of creatinine in effluent is 66.3% of total amount of creatinine in the reservoir at time zero.

For both membrane types (M150 AN69 and HF1400), the results indicate that about 5% of the total amount of creatinine (at time zero) remains in the membrane cartridge and the associated tubing. This also contributes to creatinine removal.

TABLE 1

Creatinine concentration (µg/mL) measured in ex-vivo part of Cybernetic Dialysis ™

| Time Point | Membrane | | | |
| | AN69 M150 | | HF1400 | |
| (min) | Arterial | Venous | Arterial | Venous |
| --- | --- | --- | --- | --- |
| 0 | 8.581 | NA | 8.581 | NA |
| 5 | ND | ND | 8.675 | 5.41 |
| 10 | 7.088 | 5.545 | 8.306 | 6.355 |
| 20 | 6.53 | 5.216 | 6.174 | 5.052 |
| 30 | 5.191 | 4.353 | 5.857 | 4.214 |
| 40 | 4.145 | 3.706 | 5.261 | 3.782 |
| 60 | 3.444 | 2.909 | 3.82 | 3.18 |

Figure 12:
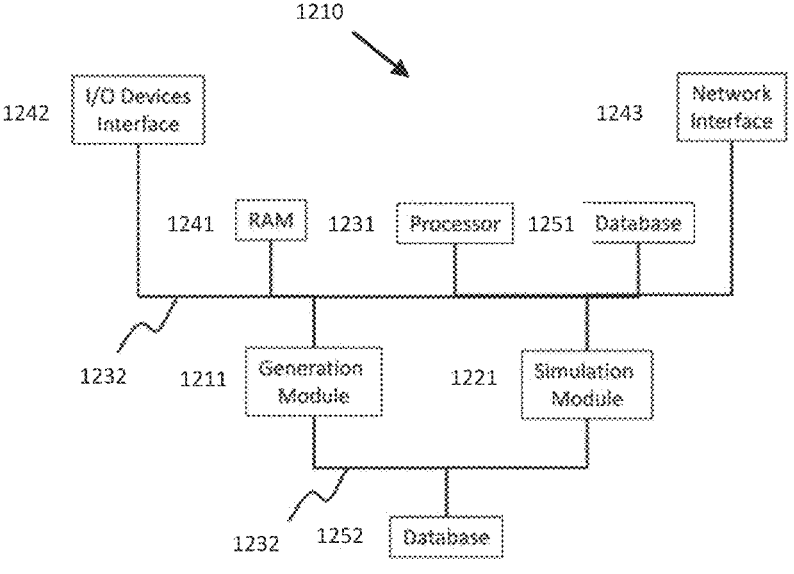
FIG. 12 is a flow diagram of a computer system in an exemplary embodiment of the invention.

Note:
AN69 M150 and HF1400 are Baxter membranes;
ND: note done;
NA: not applicable;
Time is time lapsed after start of ex-vivo dialysis Exemplary Computer System In some embodiments, the invention relates to a computer system for modeling, identifying, and predicting the effects of dialysis on drugs, medications, and chemical substances in patients. An exemplary computer system is shown schematically in FIG. 12 as computer system 1210. The computer system 1210 includes a generation module 1211, a simulation module 1221, a processor 1231, a random-access memory (RAM) 1241, an input/output interface 1242, and one or more databases, such as database 1251 and database 1252. Although two databases are shown in this exemplary embodiment, in other embodiments a single database, or more than two databases, can be employed. A bus 1232, which can include a set of hardware lines, allows transferring data and instructions among various components of the computer system. The input/output interface 1242 connects the computer system to an input/output devices, such as keyboard, mouse, display, printers, speakers, etc. Further, network interface 1244 allows the computer system 1210 to communicate with other network-enabled devices. RAM 1241 provides volatile storage for computer software instructions and data used to implement systems and methods in accordance with the invention.

The generation module 1211 generates in silico a plurality of virtual patients based on data collected from a population of previously treated patients, such as patients suffering from a health condition. The data collected from actual patients is inputted into the computer system 1210 via one or more input/out devices and stored in database 1251 and/or database 1252. The generation module 1211 accesses the stored data to generate virtual patients as mathematical constructs based on the actual patients' data. The generated virtual patients can also be stored in database 1251 and/or database 1252 and can be accessed by the simulation module 1221.

The simulation module 1221 is configured to apply a simulated therapy to the virtual patients to determine one or more physiological parameters of the virtual patients in response to the simulated therapy. The determined physiological parameters can be stored in database 1251 and/or database 1252. For example, virtual patients providing a mathematical model of the Peritoneal Dialysis Adequacy Test can be employed to determine how much urea is removed during dialysis.

The simulation module 1221 can be configured to adjust the simulated therapy based on the one or more physiological parameters to create a modified simulated therapy. The simulation module 1221 can apply the modified simulated therapy to the virtual patients and determine one or more physiological parameters of the virtual patients in response to the modified simulated therapy. The simulation module 1221 can iteratively repeat the process of modifying the therapy and determining one or more physiological parameters until an optimal therapy is obtained. For example, if an initial simulated dialysis treatment was to result in inadequate Kt/V, the duration of the dialysis and/or its frequency of administration can be increased and the Kt/V in response to this modified therapy can be determined, to decide whether additional modifications to the dialysis regimen is needed.

In some embodiments, the simulation modulation can be configured to recognize one or more physiological parameters determined in response to an applied simulated therapy that are indicative of an adverse effect.

Figure 13:
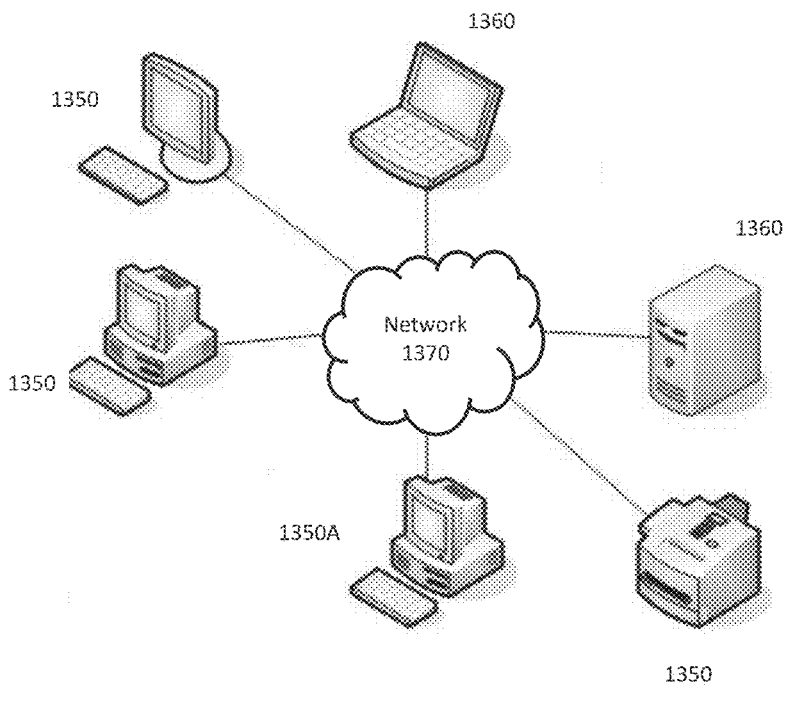
FIG. 13 is a schematic view of a computer network in an exemplary embodiment of the invention.

FIG. 13 shows an exemplary computer network in accordance with the invention. Computer(s) and/or devices 1350 and server computer(s) 1360 provide processing, storage, and input/output devices executing application programs and similar instructions. Computer(s)/devices 1350 can also be linked through communications network 1370 to other computing devices, including other devices and/or processes 1350, digital processor dialysis machines 1350A, including machines with integrated modular drug delivery devices, and server computer(s) 1360. Communications network 1370 can be part of a remote access network, a global network (e.g., the Internet), a worldwide collection of computers, Local area or Wide area networks, and gateways that currently use respective protocols (TCP/IP, Bluetooth, etc.) to communicate with one another. Other electronic device/computer network architectures are suitable.

Figure 14:
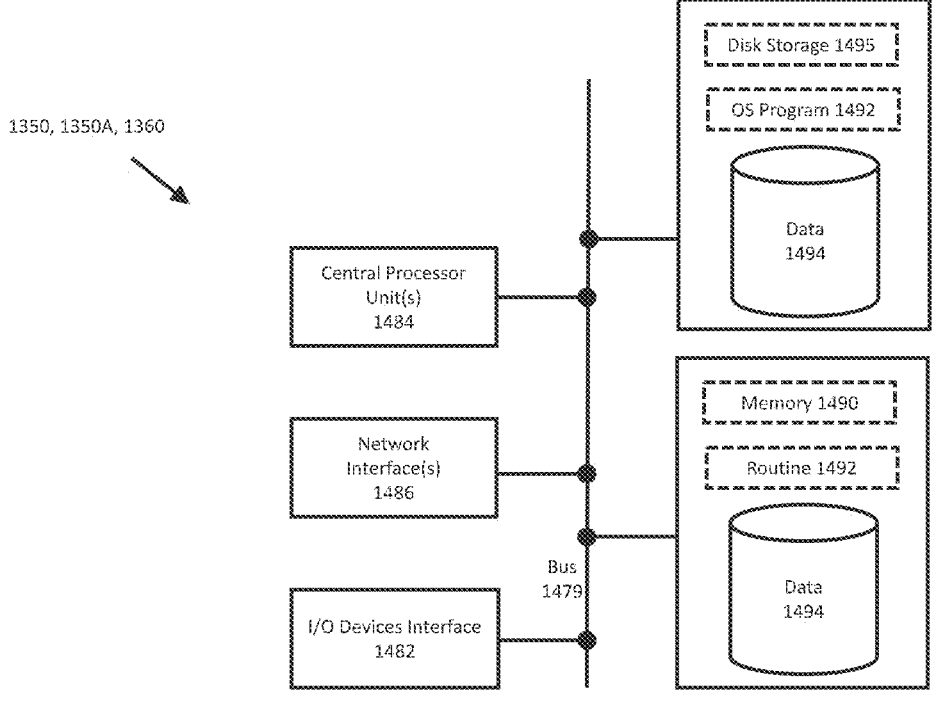
FIG. 14 is a block diagram of a computer of a network of FIG. 13.

FIG. 14 is a diagram of the internal structure of a computer (e.g., processor/device 1350, digital processor dialysis machines 1350A, or server computers 1360) in the computer system of FIG. 13. Each computer 1350, 1350A, 1360 contains a system bus 1479, where a bus is a set of hardware lines used for data transfer among the components of a computer or processing system. Bus 1479 is essentially a shared conduit that connects different elements of a computer system (e.g., processor, disk storage, memory, input/output ports, network ports, etc.) that enables the transfer of information between the elements which could be data collected during a treatment, but also instructions to a treatment simulation system and/or apparatus to follow a drug sampling arrangement provided by a central modeling engine. Attached to system bus 1479 is I/O device interface 1482 for connecting various input and output devices (e.g., keyboard, mouse, displays, printers, speakers, etc.) to the computer 1350, 1360. Network interface 1486 allows the computer to connect to various other devices attached to a network (e.g., network 1370 of FIG. 13). Memory 1490 provides volatile storage for computer software instructions 1492 and data 1494 used to implement an embodiment of the present invention. Disk storage 1495 provides non-volatile storage for computer software instructions 1492 and data 1494 used to implement an embodiment of the present invention. Central processor unit 1484 is also attached to system bus 1479 and provides for the execution of computer instructions. In one embodiment, the processor routines 1492 and data 1494 are a computer program product (generally referenced 1492), including a computer readable medium (e.g., a removable storage medium such as one or more DVD-ROM's, CDROM's, diskettes, tapes, etc.) that provides at least a portion of the software instructions for the system. Computer program product 1492 can be installed by any suitable software installation procedure, as is well known in the art. In another embodiment, at least a portion of the software instructions can also be downloaded over a cable, communication and/or wireless connection. In other embodiments, the programs are a computer program propagated signal product embodied on a propagated signal on a propagation medium (e.g., a radio wave, an infrared wave, a laser wave, a sound wave, or an electrical wave propagated over a global network such as the Internet, or other network (s)). Such carrier medium or signals provide at least a portion of the software instructions for the present routines/program 1492.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 1492 is a propagation medium that the computer system 1350 can receive and read, such as by receiving the propagation medium and identifying a propagated signal embodied in the propagation medium, as described above for computer program propagated signal product.

Overview of Results and Application of Modeling and Simulation (Virtual Patient)

Figure 10:
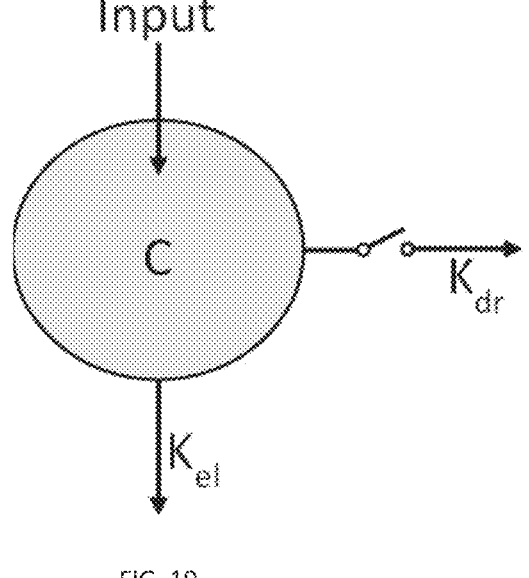
FIG. 10 is an exemplary schematic diagram of a pharmacokinetic model in accordance with the invention that was used for creatinine in treatment simulations.

FIG. 10 a schematic diagram of a pharmacokinetic model in an exemplary embodiment in accordance with the invention that was used for creatinine in treatment simulations. In the virtual patient creation (modeling and simulation) methods in accordance with the invention, the model shown in FIG. 10 was implemented in population PK (pharmacokinetic model) using NONMEM (Non-linear Mixed Effects Modeling) to simulate pharmacokinetics of creatinine as a traceable entity (or an example drug or analyte) that is administered at the given amount 200 mg (Input), assuming a 40 L volume of distribution ($V_c$), and a clearance ($K_{el}.V_c$) of 10 mL/min. Population parameters for volume and clearance were assigned a 20% CV between-subject variability. The simulations were done with and without dialysis shown as switch on/off in FIG. 10) with a dialysis rate of elimination ($K_{dr}$) that is scaled up from the ex-vivo simulated treatment using volume of distribution and blood flow. The simulations show for 24-hour continuous dialysis for both an M150 AN69 or an HF1400 membrane, more than 74% (range 60% to 88%) of creatinine is removed compared to the situation without dialysis where only 10% (range 7.5% to 12%) of creatinine is removed. This is an increase of more than 7-fold in drug removal rate per day. Clearly, this is a large dialysis effect on clearance. Such information on any analyte or drug can be generated during the research and development process and approval cycle. This knowledge can guide further design of appropriate clinical studies to allow inclusion of patients on dialysis early in research and development clinical trials. The inclusion/exclusion of patients can be individualized and decided very specifically based on individual characteristics and types of dialysis. This approach provides guidance on product labels and registration and for approval for drug administration in dialysis patients.

The same process described above for pharmacokinetic models and simulations can be implemented in physiologically based pharmacokinetic (PBPK) models or implemented as deterministic models where a single typical individual profile is simulated. The ex-vivo simulated treatment part of Cybernetic Dialysis™ can be scaled up to inform pharmacokinetic models and to enable predictions of dialysis effects and their magnitude in clinical scenarios. Exemplary embodiments of the invention used creatinine data as an example of an analyte; systems and methods in accordance with the invention (e.g., the same concept with ex-vivo dialysis, pharmacokinetic models, scaling up and simulated treatments (i.e., Cybernetic Dialysis™) can be applied to other drugs in research and development prior to registration and approval and to predict the effect of dialysis on such drugs.

The exemplary embodiments using creatinine above provide a straightforward example demonstrating the systems, methods, and efficacy of Cybernetic Dialysis™ in accordance with the invention. Creatinine has low adhesion and adsorption properties for the membrane and tubing. Other entities such as biological products (e.g., therapeutic proteins or peptides) have high adhesion and uptake in the membrane which results in large portions of the drug that stay unavailable (not returned) to plasma. Therefore, the results and scale up parameters from the ex-vivo simulated treatments in accordance with the invention are very important to ensure a compound (entity) specific prediction. For example, in the case of a therapeutic peptide, ex-vivo simulated treatments are likely to show that a large amount of drug remains in the membrane and/or tubing irreversibly, although effluent can contribute to small (or moderate) amounts of drug removal. Such predictions and confirmations the systems and methods in accordance with the invention provide guidance on dose adjustments or times of dialysis for such drugs in patients who receive dialysis.

There are hundreds of different permutations of types of dialysis, types of filters and physico-chemical properties of drugs. Therefore, there are a huge number of possible scenarios for new drugs undergoing research and development to be used in dialysis patients. There was no practical way to do clinical trials for such large numbers of possible scenarios because there are simply too many. The systems and methods in accordance with the invention can be used to study all scenarios. By using a limited number of simulated treatments ex-vivo, combined with modeling and simulation that represents extremes of dialysis membrane characteristics and interpolating or extrapolating other scenarios, and provide predictions for each possible scenario reliably.

Figure 11:
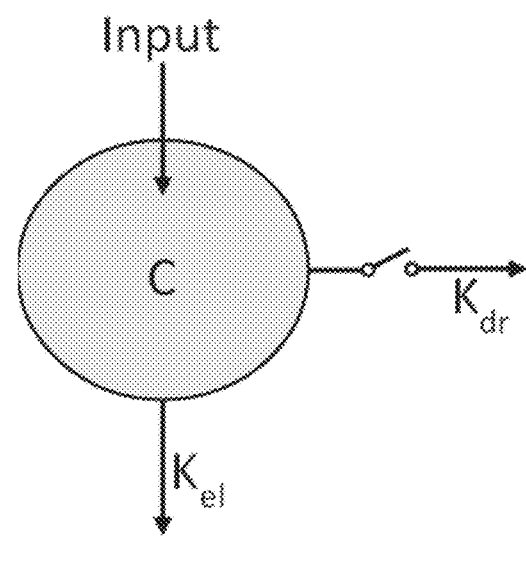
FIG. 11 is an exemplary schematic diagram of an additional pharmacokinetic model in accordance with the invention used with other drugs in treatment simulations in accordance with the invention.

The virtual patient model used for pharmacokinetics of creatinine was selected based on general data on creatinine and its physico-chemical characteristics. Other drugs may behave according to more complex distribution, absorption or pharmacokinetic principles that can be addressed and accounted for accordingly in modified pharmacokinetic models. FIG. 11 is a schematic diagram of an additional pharmacokinetic model in an exemplary embodiment of the invention that was used with other drugs in virtual patient models. For example, FIG. 11 follows a two compartmental distribution and can be used to create virtual patients for other drugs with more extensive distribution in the human body and to apply the same techniques of the invention to predict dialysis effects for creatinine.

I claim:

1. A method for determining efficacy of a dialysis therapy comprising:
   a) performing a dialysis treatment simulation for determining an amount of a drug removed by a dialysis treatment;
   wherein the dialysis treatment simulation includes:
      taking blood or plasma samples from an arterial port, a venous port, an effluent container, and a blood or plasma reservoir of a dialysis treatment simulation system; and
      determining at least one of a drug concentration, drug removal rate, drug ratio in blood or plasma, and an amount of the drug removed at each of the arterial port, the venous port, the effluent container, and the blood or plasma reservoir;
   b) generating in silico a plurality of virtual patients for modeling a health condition based on data collected from a population of previously treated patients,
   wherein the collected data represents at least one measured biological response of the previously treated patients to a previously administered therapeutic regimen of the drug,
   wherein each virtual patient includes at least one mathematical model representing a physiological system and exhibiting a one-to-one correspondence with one previously treated patient of the population of previously treated patients, and
   wherein the at least one mathematical model for each virtual patient is fitted to data of the corresponding one previously treated patient;
   c) applying the dialysis treatment simulation to the plurality of virtual patients over a simulated time period to simulate the dialysis therapy;
   d) determining one or more physiological parameters in the plurality of virtual patients in response to the applying of the dialysis treatment simulation over the simulated time period;
   e) applying at least one adjusted simulated dialysis therapy to the plurality of virtual patients over the simulated time period based on the determined one or more physiological parameters of the plurality of virtual patients;
   f) determining one or more physiological parameters in the plurality of virtual patients in response to the at least one adjusted simulated dialysis therapy over the simulated time period;
   g) determining an optimal simulated dialysis therapy from among the simulated dialysis therapy and the at least one adjusted simulated dialysis therapy, wherein determining the optimal simulated dialysis therapy includes repeating steps e) and f) until the one or more determined physiological parameters in the plurality of virtual patients are within a desired range; and
   h) recommending the optimal simulated dialysis therapy to a plurality of actual patients.

2. A dialysis treatment simulation system for determining an amount of a drug removed by a dialysis treatment comprising:
   a dialysis filter including a blood side (arterial) chamber and a dialysate side (venous) chamber;
   a plasma container containing plasma or blood spiked with the drug;
   a first sampling port for removing a first series of samples over time of the plasma or blood spiked with the drug and measuring at least one of drug concentration, drug removal rate, drug ratio in the blood or plasma, and an amount of the drug removed of each of the first series of samples over time of the plasma or blood spiked with the drug;

a plasma or blood pump for moving the plasma or blood to an input of the blood side (arterial) chamber of the dialysis filter;

a second sampling port at the input of the blood side (arterial) chamber of the dialysis filter for removing a second series of samples over time of the plasma or blood spiked with the drug and measuring at least one of drug concentration, drug removal rate, drug ratio in the blood or plasma, and an amount of the drug removed of each of the second series of samples over time of the plasma or blood spiked with the drug;

a membrane for separating the blood side (arterial) chamber of the dialysis filter from the dialysate side (venous) chamber of the dialysis filter and for removing waste products from the plasma or blood spiked with the drug;

a third sampling port at the output of the blood side (arterial) chamber of the dialysis filter for removing a third series of samples over time of the plasma or blood spiked with the drug passed through the blood side (arterial) chamber of the dialysis filter and measuring at least one of drug concentration, drug removal rate, drug ratio in the blood or plasma, and an amount of the drug removed of each of the third series of samples over time of the plasma or blood spiked with the drug passed through the blood side (arterial) chamber of the dialysis filter;

a dialysate reservoir container containing dialysate;

a dialysate pump for moving the dialysate from the dialysate reservoir container to an input of the dialysate side (venous) chamber, wherein the dialysate carries the waste products from the plasma or blood spiked with the drug to an output of the dialysate side (venous) chamber;

an effluent pump for receiving the dialysate with the waste products in the form of effluent fluid and for moving the effluent fluid from the output of the dialysate side (venous) chamber to an effluent container; and a fourth sampling port for removing a series of samples over time of the effluent fluid from the effluent container and for removing a fourth series of samples over time of the plasma or blood spiked with the drug from the effluent fluid and measuring at least one of drug concentration, drug removal rate, drug ratio in the blood or plasma, and an amount of the drug removed of each of the fourth series of samples over time of the plasma or blood spiked with the drug, wherein the amount of the drug removed by the dialysis treatment is determined by comparing measurements of a change in the first series of samples, the second series of samples, the third series of samples, and the fourth series of samples.

3. A computer system for determining an efficacy of a therapy comprising:

a processor configured to:

a) perform a dialysis treatment simulation for determining at least one of a total amount of or a rate of a drug removed by a dialysis treatment;

wherein the dialysis treatment simulation includes:

taking a series of blood or plasma samples over time from an arterial port, a venous port, an effluent container, and a blood or plasma reservoir of a dialysis treatment simulation system; and determining at least one of a drug concentration, drug removal rate, drug ratio in blood or plasma, and an amount of the drug removed at each of the arterial port, the venous port, the effluent container, and the blood or plasma reservoir;

b) generate in silico a plurality of virtual patients for modeling a health condition based on data collected from a population of previously treated patients having the health condition, wherein the collected data represents at least one measured biological response of the previously treated patients to a previously administered therapeutic regimen of the drug, wherein each virtual patient includes at least one mathematical model representing a physiological system and exhibiting a one-to-one correspondence with one previously treated patient of the population of previously treated patients, and wherein the at least one mathematical model for each virtual patient is fitted to data of the corresponding one previously treated patient;

c) apply the dialysis treatment simulation to the plurality of virtual patients over a simulated time period to simulate dialysis therapy;

d) determine one or more physiological parameters in the plurality of virtual patients in response to the applied dialysis treatment simulation over the simulated time period;

e) apply at least one adjusted simulated dialysis therapy to the plurality of virtual patients over the simulated time period based on the determined one or more physiological parameters of the plurality of virtual patients;

f) determine an optimal simulated dialysis therapy from among the simulated dialysis therapy and the at least one adjusted simulated dialysis therapy by iteratively performing the following steps until the determined one or more physiological parameters in the plurality of virtual patients are within a desired range:

applying the at least one adjusted simulated dialysis therapy to the plurality of virtual patients over the simulated time period based on the determined one or more physiological parameters of the plurality of virtual patients; and determining one or more physiological parameters in the plurality of virtual patients in response to the at least one adjusted simulated dialysis therapy over the simulated period of time; and g) recommend the optimal simulated therapy for application to a plurality of actual patients.

* * * * *